(12) United States Patent
Saleeb

(10) Patent No.: US 11,793,589 B2
(45) Date of Patent: Oct. 24, 2023

(54) SURGICAL INSTRUMENT STAND

(71) Applicant: Samuel Saleeb, Suffolk, VA (US)

(72) Inventor: Samuel Saleeb, Suffolk, VA (US)

(*) Notice: Subject to any disclaimer, the term of this patent is extended or adjusted under 35 U.S.C. 154(b) by 333 days.

(21) Appl. No.: 17/203,339

(22) Filed: Mar. 16, 2021

(65) Prior Publication Data

US 2022/0296327 A1 Sep. 22, 2022

(51) Int. Cl.
*A47F 5/04* (2006.01)
*A61B 50/24* (2016.01)

(52) U.S. Cl.
CPC .......... *A61B 50/24* (2016.02); *A47F 5/04* (2013.01); *A61B 2560/04* (2013.01)

(58) Field of Classification Search
CPC .......... A61G 50/24; A61G 2560/04; A61G 2050/21; A61G 50/26; A47F 5/04; A47F 5/05; A47G 25/0692
USPC ......... 211/85.13, 197, DIG. 1, 66, 124, 123, 211/193, 204; 248/215, 129, 122.1, 214, 248/206.5
See application file for complete search history.

(56) References Cited

U.S. PATENT DOCUMENTS

| | | | | |
|---|---|---|---|---|
| 896,990 A * | 8/1908 | Hill | ........................ | F16M 11/00 211/196 |
| 1,211,527 A * | 1/1917 | Berndt | ................. | A47B 23/046 248/231.71 |
| 1,795,296 A * | 3/1931 | De Zeng | ................ | A61B 50/20 211/85.13 |
| 2,630,922 A * | 3/1953 | Hess | ................... | A47G 25/0664 108/28 |
| 2,965,235 A * | 12/1960 | Daline | .................. | A47F 5/0823 211/DIG. 1 |
| 3,483,494 A * | 12/1969 | Cromie | .................. | A61B 46/23 428/164 |
| 3,776,387 A * | 12/1973 | Brent | ..................... | A61B 50/20 211/DIG. 1 |
| 4,690,285 A * | 9/1987 | Stone | ................... | B43M 99/008 248/442.2 |
| 5,022,538 A * | 6/1991 | Richmond | ........... | A47F 5/0876 211/85.15 |
| 5,038,946 A * | 8/1991 | Tenser | ................. | A47F 5/0093 211/163 |
| 5,143,231 A * | 9/1992 | Chang | ................. | A47B 96/061 211/96 |
| 5,163,566 A * | 11/1992 | Hempel | ................... | A47K 1/09 211/DIG. 1 |
| 5,319,816 A * | 6/1994 | Ruehl | ................... | A61G 7/0509 5/600 |
| 5,435,448 A * | 7/1995 | Kempen | ................ | A61B 50/20 206/370 |
| 5,509,545 A * | 4/1996 | Banke | ................ | A47G 25/0671 211/205 |
| 5,630,517 A * | 5/1997 | Maznik | ................ | F16M 11/041 211/DIG. 1 |
| 5,692,615 A * | 12/1997 | Fischer | .................. | A61B 90/90 211/89.01 |

(Continued)

*Primary Examiner* — Jennifer E. Novosad

(57) ABSTRACT

A surgical stand may include a vertical pole portion with a securing clamp junction holding a horizontal pole in a fixed position with respect to the vertical pole, and the horizontal pole includes a plate interface including a number of securing mechanisms for holding surgical instruments against the plate interface, and a number of rings disposed along the horizontal pole on both sides of the plate interface.

6 Claims, 4 Drawing Sheets

(56) References Cited

U.S. PATENT DOCUMENTS

| | | | | |
|---|---|---|---|---|
| 5,833,081 A * | 11/1998 | Smith | ................. | B60R 7/10 224/313 |
| 6,065,618 A * | 5/2000 | Stetler | ................. | A47B 61/003 211/205 |
| 6,155,439 A * | 12/2000 | Draughn | ................. | A61B 50/22 211/85.13 |
| 6,390,311 B1 * | 5/2002 | Belokin | ................. | A61M 5/1415 248/129 |
| 6,494,327 B2 * | 12/2002 | Huang | ................. | F16M 11/28 211/205 |
| 6,530,491 B2 * | 3/2003 | Brehmer | ................. | A47B 57/26 211/205 |
| 6,629,615 B2 * | 10/2003 | Kim | ................. | F16L 3/223 211/85.13 |
| 7,143,902 B2 * | 12/2006 | Iversen | ................. | B60R 7/10 211/85.3 |
| 7,874,410 B2 * | 1/2011 | Fulbrook | ................. | A61M 5/1415 361/111 |
| 8,016,134 B1 * | 9/2011 | Templin | ................. | F16M 11/06 211/85.7 |
| 8,020,716 B2 * | 9/2011 | Vitale | ................. | A47F 5/04 211/205 |
| 8,172,188 B2 * | 5/2012 | Dubinskiy | ................. | B62J 9/23 248/221.11 |
| 8,403,275 B2 * | 3/2013 | Cote | ................. | A61M 5/1415 248/125.7 |
| 8,789,713 B2 * | 7/2014 | Koller | ................. | A47F 7/0028 211/74 |
| 9,033,162 B2 * | 5/2015 | Brotzman | ................. | A61B 50/20 211/126.14 |
| 9,949,554 B2 * | 4/2018 | Sullivan | ................. | A45D 44/06 |
| 10,383,697 B2 * | 8/2019 | Karasina | ................. | A61B 50/15 |
| D880,568 S * | 4/2020 | Gorsuch | ................. | D8/382 |
| 11,116,596 B2 * | 9/2021 | Stevens | ................. | A61B 50/26 |
| 11,432,984 B2 * | 9/2022 | Hanlan | ................. | A61G 15/16 |
| 2001/0007343 A1 * | 7/2001 | McElhaney, Jr. | ................. | B25H 5/00 248/211 |
| 2003/0089830 A1 * | 5/2003 | Loughman | ................. | F16M 11/10 248/125.7 |
| 2006/0054576 A1 * | 3/2006 | Durham | ................. | F26B 25/06 211/85.7 |
| 2009/0008347 A1 * | 1/2009 | Bell | ................. | A47F 5/02 211/183 |
| 2010/0090071 A1 * | 4/2010 | Gothard | ................. | B05B 13/0285 248/129 |
| 2014/0209550 A1 * | 7/2014 | Pryor | ................. | A61M 5/1417 211/85.13 |
| 2015/0285428 A1 * | 10/2015 | Duperron | ................. | F16M 11/245 248/163.1 |
| 2015/0328397 A1 * | 11/2015 | Bally | ................. | A47F 5/06 29/434 |
| 2016/0000993 A1 * | 1/2016 | Endyk | ................. | A61M 5/1782 211/85.13 |
| 2022/0296327 A1 * | 9/2022 | Saleeb | ................. | A61B 50/24 |

\* cited by examiner

SURGICAL INSTRUMENT STAND

TECHNICAL FIELD

This application relates to a surgical tool stand, and in particular, a surgical instrument tool stand with a customizable interface portion to accommodate the specific requirements of a surgeon during a surgical procedure.

BACKGROUND

Conventional surgeries are performed in an operating room ("OR"). The protocol for preparing a surgeon and his or her surgical team requires the utmost care and diligence to avoid infection to the patient. Conventionally, surgical instruments, such as, clamps, retractors, forceps, suture ties, containers, and towels, are all sterile and carefully introduced onto the sterile field of the OR. Some instruments may even require power often provided by receptables mounted in the ceiling or floor.

Historically, the items that may be brought into an OR are limited by the slowly changing field of surgery in general. Over time, the surgical instruments have evolved to include various different shapes and materials, however, for the majority of surgical items, very little has changed over the years. One example of a conventional OR setup may include lint free towels draped across the mayo stand, suture ties, various cutting instruments, which may be selected by a surgical technician for the surgeon. The position and location of the tools are always further away from the patient than they could be during the surgical procedure. Every second counts during a procedure and the surgeon's ability to identify and select a tool as quickly as possible may be critical to the success of the surgery.

SUMMARY

Example embodiments of the present application disclose an apparatus including a vertical pole portion with a securing clamp junction holding a horizontal pole in a fixed position with respect to the vertical pole, the horizontal pole comprises a plate interface comprising a plurality of securing mechanisms for holding surgical instruments against the plate interface, and a plurality of rings disposed along the horizontal pole on both sides of the plate interface.

BRIEF DESCRIPTION OF THE DRAWING(S)

DETAILED DESCRIPTION

It will be readily understood that the components of the present application, as generally described and illustrated in the figures herein, may be arranged and designed in a wide variety of different configurations. Thus, the following detailed description of the embodiments of a method and apparatus, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

Figure 1:
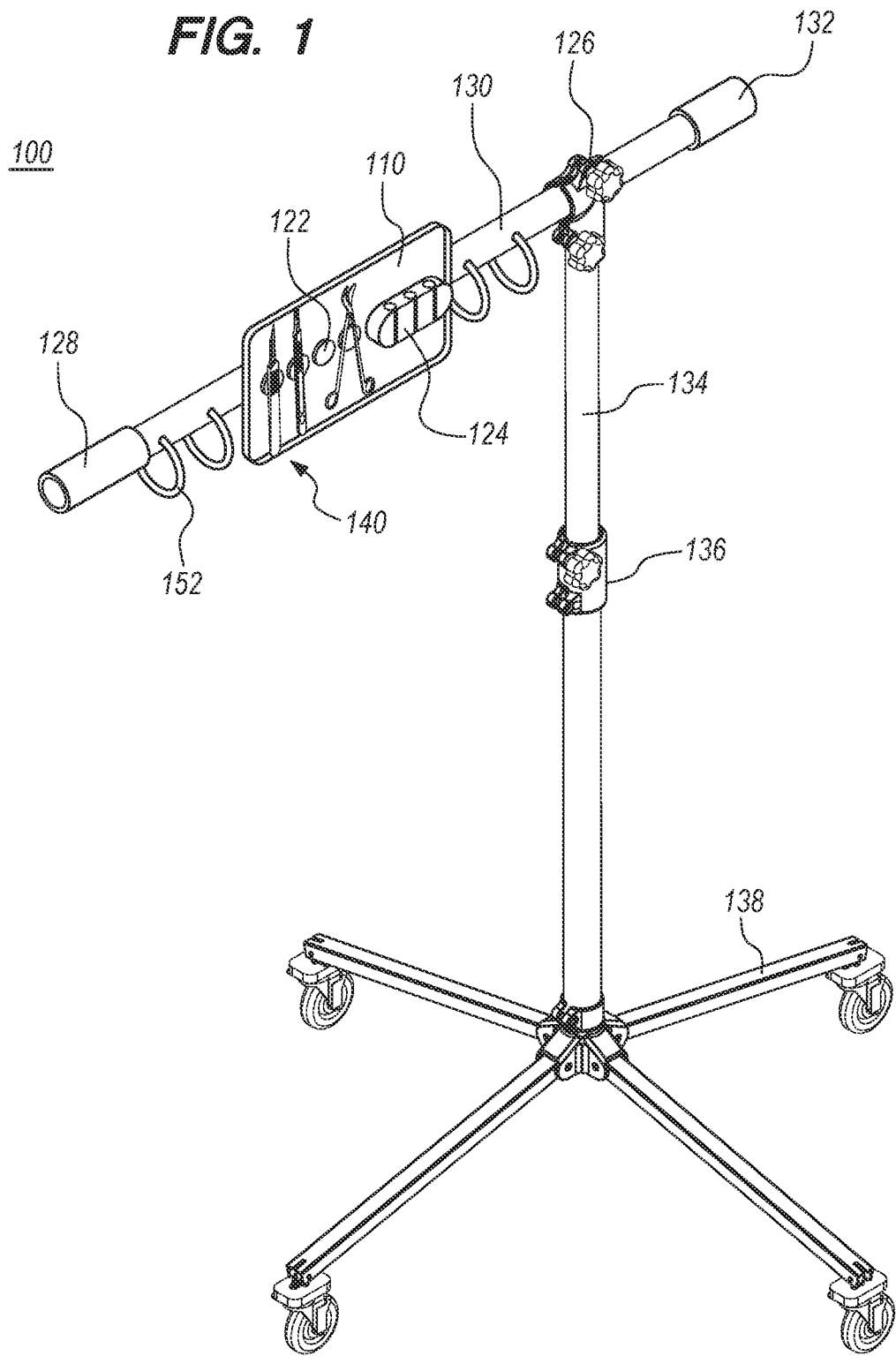
FIG. 1 illustrates a front view angled perspective of the surgery stand in an assembled position, in accordance with example embodiments.

FIG. 1 illustrates a front view angled perspective of the surgery stand in an assembled position, in accordance with example embodiments. Referring to FIG. 1, the surgery instrument configuration 100 includes a support base 138, which may be fixed position pegs, or may include wheels as illustrated in FIG. 1. The exterior vertical pole may be larger than the interior vertical pole 134 which can move into and out of the body of the exterior pole and be kept in a tight secure position via the adjustable clamp 136. The interior pole 134 may also end at another pole junction with another adjustable clamp or pairs of clamps 126 with a pass-through slot for a horizontal pole 130 to pass-through and be secured via yet the another adjustable clamp 126. The junction may also be a slot junction plate that has pass-through slots in an orthogonal configuration so the vertical pole 134 and the horizontal pole 130 can meet at the junction point and maintain a steady position in an orthogonal configuration with respect to one another.

The horizontal pole 130 may be part of a sanitation kit that is packaged in a sanitized container and which comes with all the components on the horizontal pole 130 illustrated in FIG. 1. The kit can be opened and assembled out of a sterile container and placed at a horizontal position with respect to the vertical stand portion. Alternatively, the sanitary components which are sterilized prior to any surgical procedure may just be the tool plate interface 110 while the pole 130, the end caps 128 and 132 and the permanently fixed cord holding rings 152, are maintained and recycled from past procedures and sterilized manually while the other portions are new and removed from sterile containers each time.

The tool plate interface 110 may include a set of magnets 122, such as three of four or more magnets, or a fixed length magnetic strip that traverses from one portion of the tool plate interface 110 to another. The magnets or magnetic strip may occupy approximately 50 percent of the tool plate interface width, while the second half of the plate width is reserved for push-fitted formed slots 124 which are made of a collapsible material that deforms and permits items 140, such as surgical tools and attachments to be wedged inside the slots of the push-fitted pad 124 by a gentle force. The rings 152 may include one, two, three or more on each side of the pole 130. A surgical instrument with an electric wire charge, such as a cauterization tool that mends human tissue during cutting and sewing operations may be rested on the plate 110 via the form-fitted press slots 124 and/or the magnet 122. The wire may pass through the rings 152 on either side of the pole 130.

Figure 2:
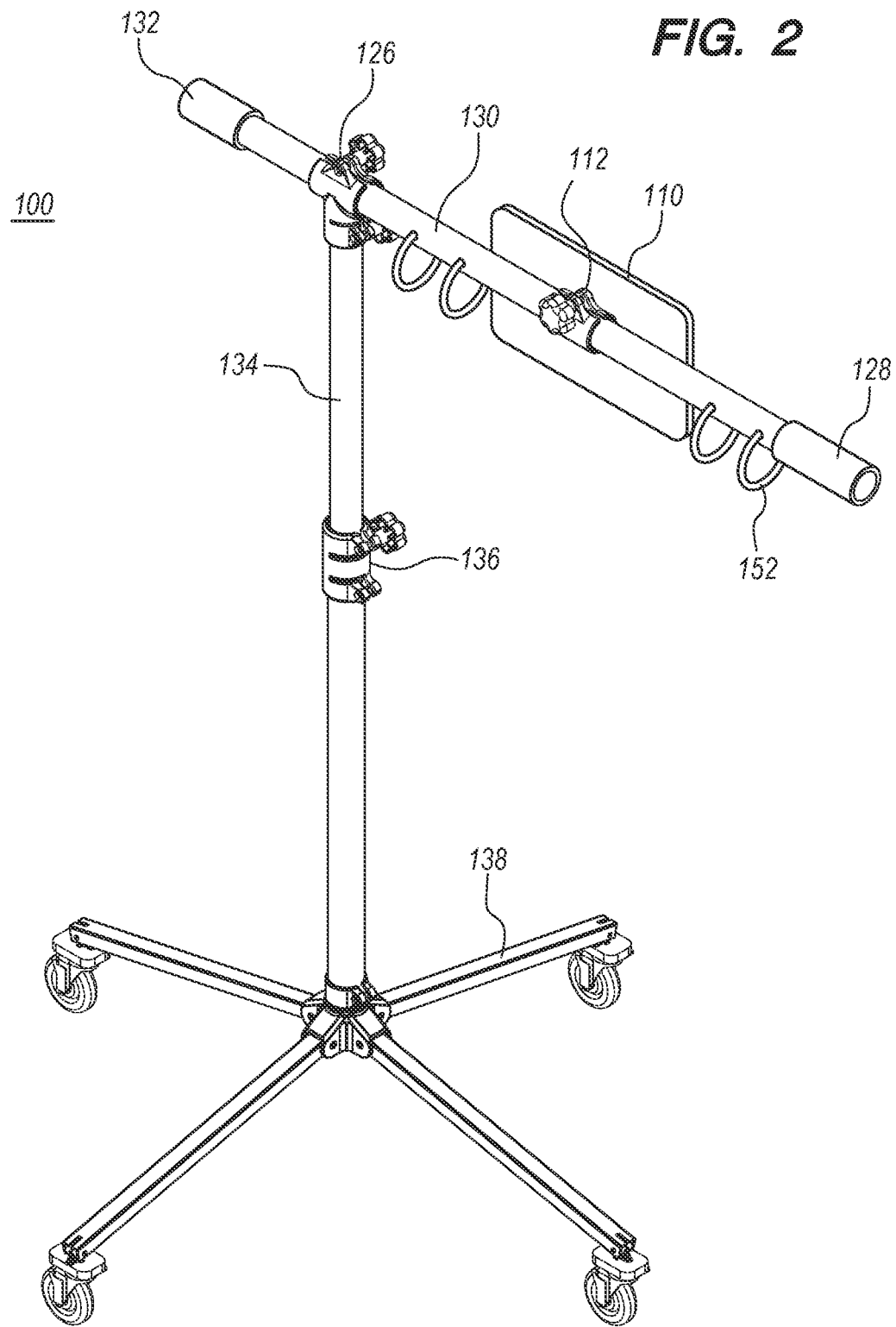
FIG. 2 illustrates a rear-view angled perspective of the surgery stand in an assembled position, in accordance with example embodiments.

FIG. 2 illustrates a rear-view angled perspective of the surgery stand in an assembled position, in accordance with example embodiments. Referring to FIG. 2, the rear view demonstrates the removability and ease of operation of the securing tab and adjustable clamp 112. The tool plate interface 110 may be quickly secured to the horizontal pole 130 prior to performing a procedure. The rings 152 can offer a securing mechanism for electrical wires attached to electrical tools which have their cords attached to receptacles in the ceiling or floor. The rings 152 offer a way to have the cords away from the patient body during a procedure.

Figure 3:
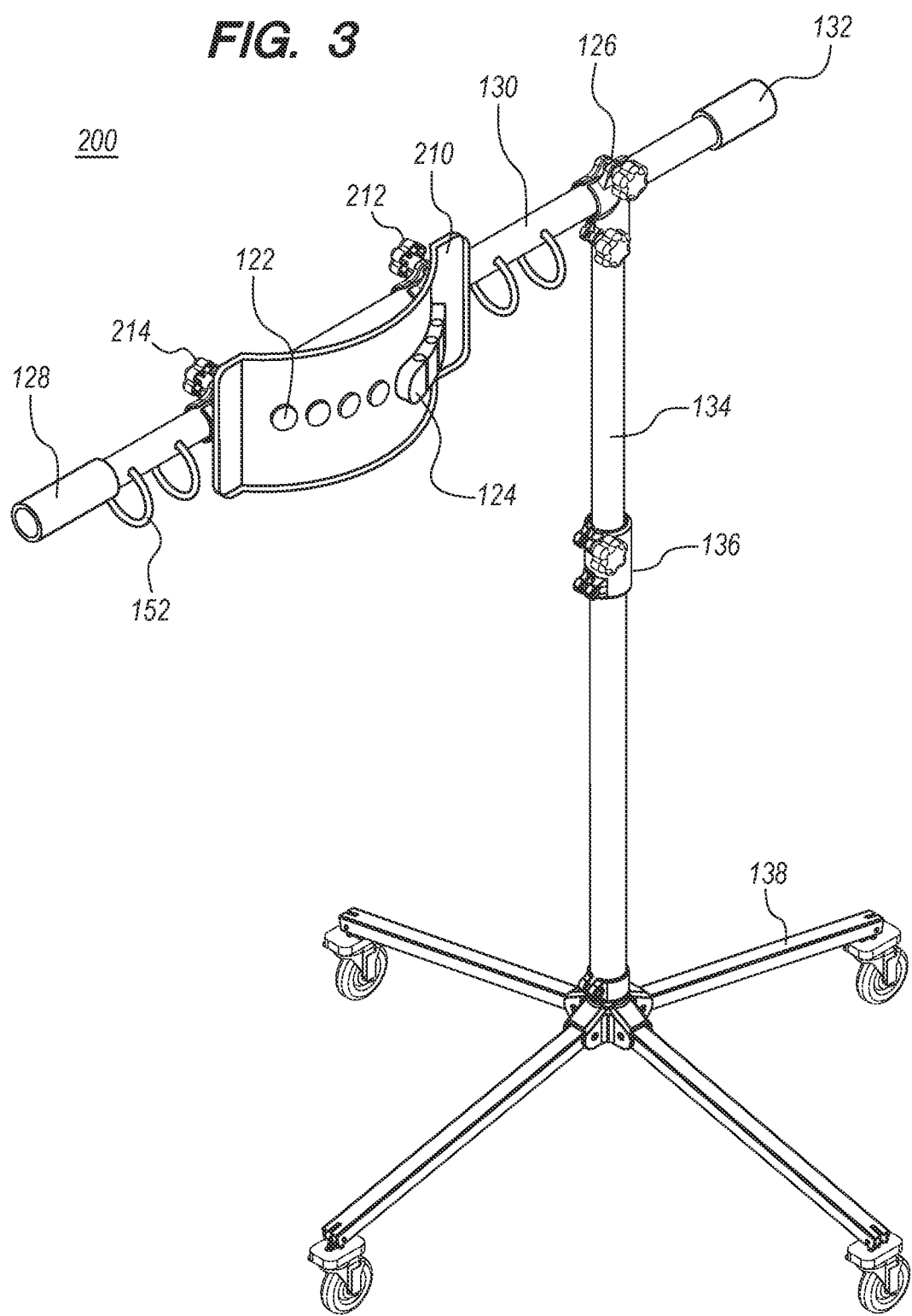
FIG. 3 illustrates a front view angled perspective of the surgery stand with a bowed tool interface plate in an assembled position, in accordance with example embodiments.

FIG. 3 illustrates a front view angled perspective of the surgery stand with an 'arced'/'arched' or 'bowed' tool interface plate in an assembled position, in accordance with example embodiments. Referring to FIG. 3, in this configuration 200, the tool plate interface 212 is angled/bowed outward towards the user to provide a closer position for the tools which are hung or placed on the plate 210. The number of magnets 122 or push-fitted slots 124 may be larger than the previous configuration since the bowed plate 210 has a larger surface area than the flat plate 110. However, in this example illustrations of FIG. 3, the number of magnets and push-fitted slots is the same. The larger bowed plate 210 does not make contact at the center, so there are two clamps on respective ends 212 and 214 to hold the plate onto the horizontal pole 130.

Figure 4:
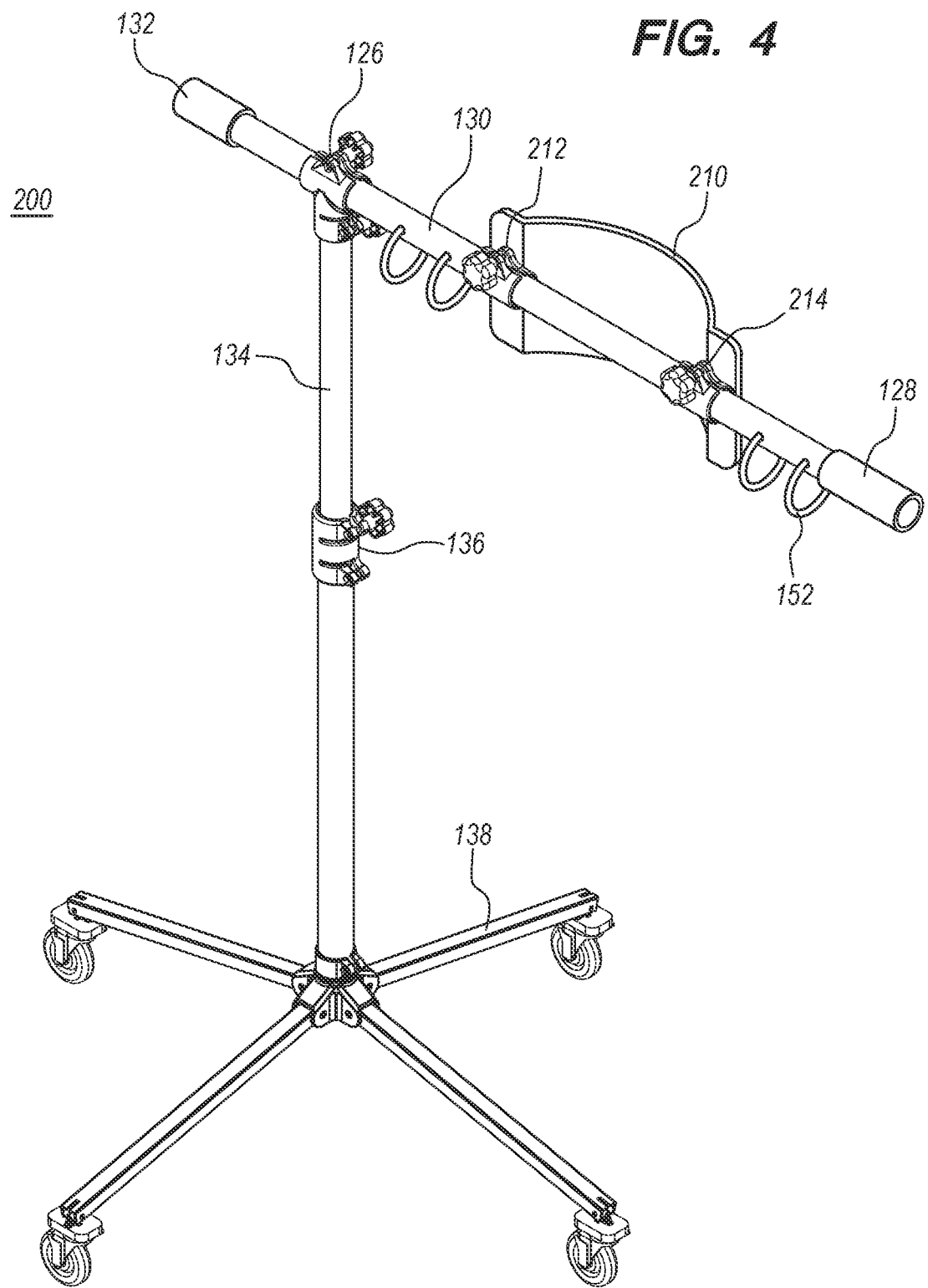
FIG. 4 illustrates a rear-view angled perspective of the surgery stand with a bowed tool interface plate in an assembled position, in accordance with example embodiments.

FIG. 4 illustrates a rear-view angled perspective of the surgery stand with a bowed tool interface plate in an assembled position, in accordance with example embodiments. Referring to FIG. 4, the ends of the bowed shaped plate 210 may have a flat portion that includes two clamp screw interfaces where the clamp screws 212 and 214 can be mounted against the pole 130 in a secured position.

In both examples of FIGS. 1-2 and 3-4, the plate may have holes, such as a series of eight (or 4, 6 or 10) holes (not shown), so the surgeon can customize the number of magnets or form-fitted slots to include on the available surface area of the interface plate 110/210. For example, the user may desire to have eight magnetic elements 122 or all form-fitted slots 124. The form-fitted push slots may be placed as a block of slots into three or four holes at a time. The magnets may occupy one hole at a time as each magnet may have a corresponding peg on the rear side. Both of the element types may be placed on the interface plate 110/210 via pegs that are disposed on the rear of those elements and which are placed into the holes of the plate. Also, the plate may have magnets or VELCRO to secure the elements to the plate. This configuration provides a wide variety of options, such as alternating between magnets and push slots along the face plate area depending on the desires of the user.

One example embodiment may include a vertical pole portion with a securing clamp junction holding a horizontal pole in a fixed position with respect to the vertical pole, and the horizontal pole includes a plate interface with a plurality of securing mechanisms for holding surgical instruments against the plate interface, and a plurality of rings disposed along the horizontal pole on both sides of the plate interface. The securing mechanisms include a plurality of magnets and a plurality of form-fitted slots. The plurality of magnets include 3-6 magnets and the plurality of form-fitted slots comprises 3-6 form-fitted slots. The plurality of magnets occupy approximately half the width of the plate interface and the plurality of form-fitted slots occupy approximately a second half of the width of the plate interface. The plurality of rings are embedded into the body of the horizontal pole. The plurality of rings include two rings on a first half of the length of the horizontal pole and two additional rings on a first half of the length of the horizontal pole. The plate interface may include between 4 and 10 holes which receive pegs affixed to the backs of the securing mechanisms.

It will be readily understood that the components of the invention, as generally described and illustrated in the figures herein, may be arranged and designed in a wide variety of different configurations. Thus, the detailed description of the embodiments is not intended to limit the scope of the invention as claimed, but is merely representative of selected embodiments of the invention.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention.

While preferred embodiments of the present application have been described, it is to be understood that the embodiments described are illustrative only and the scope of the application is to be defined solely by the appended claims when considered with a full range of equivalents and modifications thereto.

What is claimed is:

1. An apparatus comprising:
   a vertical pole with a securing clamp junction holding a horizontal pole in a fixed position with respect to the vertical pole;
   wherein the horizontal pole comprises
   a curved plate with two flat surface portions on either end of the curved plate, wherein the curved plate comprises
      a plurality of securing mechanisms for holding surgical instruments against a bowed portion of the curved plate,
      a plurality of plate securing clamps affixed to the respective flat surface portions of the curved plate; and
      a plurality of rings disposed along the horizontal pole on both sides of the plate interface.

2. The apparatus of claim 1, wherein the securing mechanisms comprise a plurality of magnets and a plurality of form-fitted slots.

3. The apparatus of claim 2, wherein the plurality of magnets comprises 3-6 magnets and the plurality of form-fitted slots comprises 3-6 form-fitted slots.

4. The apparatus of claim 3, wherein the plurality of magnets are disposed on a first half of a surface area of the curved plate and the plurality of form-fitted slots are disposed on a second half of the surface area of the curved plate.

5. The apparatus of claim 1, wherein the plurality of rings are embedded into a body of the horizontal pole.

6. The apparatus of claim 5, wherein the plurality of rings comprise two rings on a first half of the length of the horizontal pole and two additional rings on a first half of the length of the horizontal pole.

* * * * *